United States Patent
Fujii

(10) Patent No.: US 10,888,388 B2
(45) Date of Patent: Jan. 12, 2021

(54) MEDICAL-MANIPULATOR ROTATION MECHANISM

(71) Applicant: OLYMPUS CORPORATION, Tokyo (JP)

(72) Inventor: Masahiro Fujii, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 179 days.

(21) Appl. No.: 16/147,959

(22) Filed: Oct. 1, 2018

(65) Prior Publication Data

US 2019/0029768 A1 Jan. 31, 2019

Related U.S. Application Data

(63) Continuation of application No. PCT/JP2016/061239, filed on Apr. 6, 2016.

(51) Int. Cl.
| | |
|---|---|
| *A61B 34/00* | (2016.01) |
| *A61B 17/29* | (2006.01) |
| *A61B 34/30* | (2016.01) |

(52) U.S. Cl.
CPC .......... *A61B 34/71* (2016.02); *A61B 17/29* (2013.01); *A61B 34/30* (2016.02); *A61B 2017/2905* (2013.01); *A61B 2017/2929* (2013.01); *A61B 2034/301* (2016.02); *A61B 2034/305* (2016.02); *A61B 2034/715* (2016.02)

(58) Field of Classification Search
CPC ........ A61B 2090/061; A61B 2034/715; A61B 2034/301; A61B 2017/2929; A61B 2017/2905; A61B 2017/2903; A61B 17/29; A61B 17/00327; A61B 34/71; A61B 34/30

See application file for complete search history.

(56) References Cited

U.S. PATENT DOCUMENTS

| | | |
|---|---|---|
| 6,746,443 B1 | 6/2004 | Morley et al. |
| 6,902,560 B1 | 6/2005 | Morley et al. |
| 2003/0100892 A1 | 5/2003 | Morley et al. |
| 2005/0204851 A1 | 9/2005 | Morley et al. |
| 2008/0103492 A1 | 5/2008 | Morley et al. |

(Continued)

FOREIGN PATENT DOCUMENTS

| | | |
|---|---|---|
| EP | 2415408 A1 | 2/2012 |
| EP | 2532314 A1 | 12/2012 |

(Continued)

OTHER PUBLICATIONS

International Search Report dated Jul. 5, 2016 issued in PCT/JP2016/061239.

*Primary Examiner* — George J Ulsh

(74) *Attorney, Agent, or Firm* — Scully, Scott, Murphy & Presser, P.C.

(57) ABSTRACT

A medical-manipulator rotation mechanism includes: a cylindrical rotator that is fixed to a treatment part at the distal end and that is supported so as to be rotatable about the longitudinal axis; a long power-transmitting member wound around the rotator; and a folding part that bends the power-transmitting member led out in a tangential direction from the rotator and guides the power-transmitting member toward the proximal-end side, wherein the power-transmitting member is led out in tangential directions at different positions between which a wound part of the rotator around which the power-transmitting member is wound exists.

11 Claims, 7 Drawing Sheets

(56) References Cited

U.S. PATENT DOCUMENTS

| | | |
|---|---|---|
| 2011/0213346 A1 | 9/2011 | Morley et al. |
| 2012/0022509 A1 | 1/2012 | Naito |
| 2012/0303003 A1 | 11/2012 | Naito |
| 2014/0052156 A1 | 2/2014 | Morley et al. |
| 2016/0022366 A1 | 1/2016 | Morley et al. |

FOREIGN PATENT DOCUMENTS

| | | |
|---|---|---|
| JP | 2009-142513 A | 7/2009 |
| WO | WO 2011/108142 A1092011 | 9/2011 |
| WO | WO 2012/056884 A1 | 5/2012 |

MEDICAL-MANIPULATOR ROTATION MECHANISM

CROSS-REFERENCE TO RELATED APPLICATIONS

This is a continuation of International Application PCT/JP2016/061239 which is hereby incorporated by reference herein in its entirety.

TECHNICAL FIELD

The present invention relates to a medical-manipulator rotation mechanism.

BACKGROUND ART

A known medical manipulator has a rotation mechanism that rotates a treatment part at the distal end thereof about the longitudinal axis (for example, see Patent Literature 1).

In this medical manipulator, two wires are wound, in the circumferential direction, around a cylindrical rotation part that is fixed to the treatment part at the distal end and that is rotatable about the longitudinal axis. The wires, which are led out in tangential directions of the cylindrical part, are bent in the longitudinal direction by pulleys, which are supported at the sides of the rotation part so as to be rotatable about an axis perpendicular to the longitudinal axis, and are guided toward the proximal-end side.

CITATION LIST

Patent Literature

{PTL 1} U.S. Pat. No. 6,746,443

SUMMARY OF INVENTION

An aspect of the present invention is a medical-manipulator rotation mechanism including: a cylindrical rotator that is fixed to a treatment part at a distal end and that is supported so as to be rotatable about a longitudinal axis; a long power-transmitting member wound around the rotator; and a folding part that bends the power-transmitting member led out in a tangential direction from the rotator to guide the power-transmitting member toward a proximal-end side. The power-transmitting member is led out in tangential directions at different positions between which a wound part of the rotator around which the power-transmitting member is wound exists.

DESCRIPTION OF EMBODIMENTS

A rotation mechanism 8 of a medical manipulator 1 according to an embodiment of the present invention will be described below with reference to the drawings.

Figure 1:
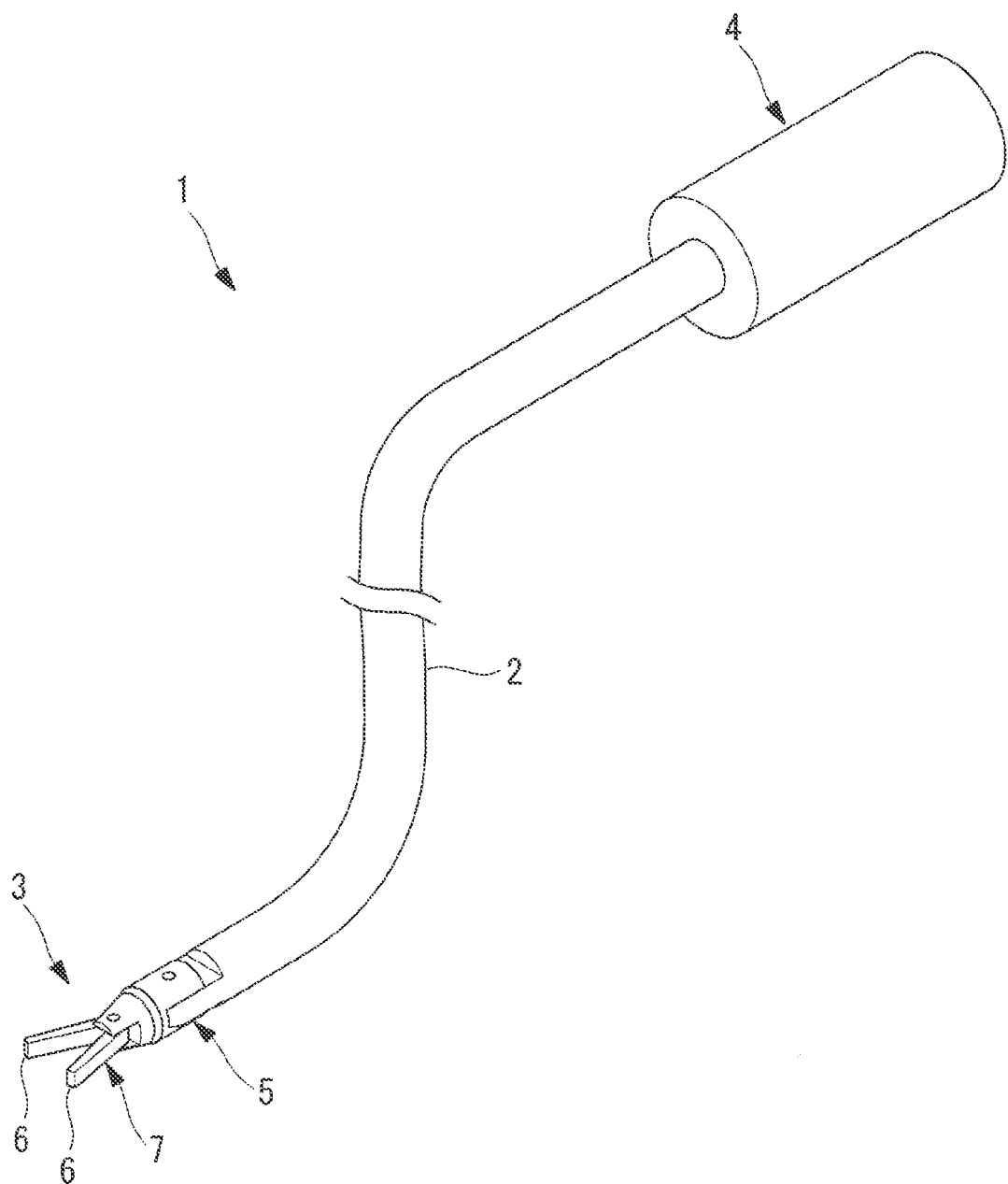
FIG. 1 is a diagram showing the overall configuration of a medical manipulator having a rotation mechanism according to an embodiment of the present invention.

As shown in FIG. 1, the medical manipulator 1 according to this embodiment includes: an elongated flexible insertion part 2; a movable part 3 disposed at the distal end of the insertion part 2; a driving part 4 disposed at the proximal-end side of the insertion part 2; and a power-transmitting member (see FIG. 2) that transmits the power from the driving part 4 to the movable part 3. The power-transmitting member is, for example, a wire 10.

Figure 2:
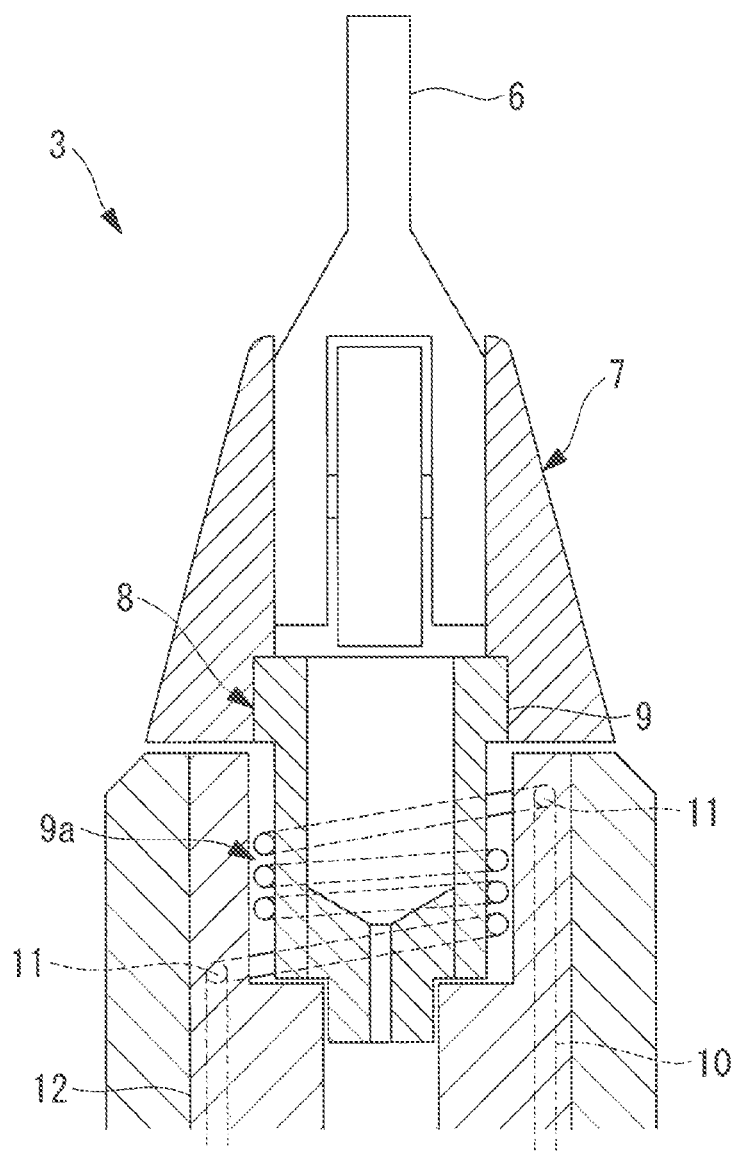
FIG. 2 is a vertical sectional view showing a movable part provided at the distal end of the medical manipulator in FIG. 1.

As shown in FIGS. 1 and 2, the movable part 3 includes, at the distal end of a bending joint 5 provided so as to be pivotable about an axis perpendicular to the longitudinal axis: a gripping part (treatment part) 7 having a pair of gripping pieces 6, which are opened and closed; and a rotation mechanism 8 according to this embodiment that rotates the gripping part 7 about the longitudinal axis. The bending joint 5 may be omitted.

As shown in FIG. 2, the rotation mechanism 8 according to this embodiment includes a cylindrical rotator 9 fixed to the gripping part 7, the wire 10 wound on the outer surface of the rotator 9, and folding parts 11 that bend portions of the wire 10 that are led out in tangential directions from the rotator 9 and guide the wire portions toward the proximal-end side in the longitudinal axis direction.

A substantially cylindrical housing (outer member) 12 is fixed to the distal end of a bracket constituting the bending joint 5. The rotator 9 is supported in the housing 12 so as to be rotatable about the longitudinal axis. The rotator 9 has a wound part 9a, around which the wire 10 is spirally wound over a predetermined area in the longitudinal axis direction. The wire 10 is fixed to the rotator 9 at substantially the middle position of the wound part 9a.

The wire 10 wound around the wound part 9a is led out in tangential directions of the rotator 9 at both sides of the wound part 9a in the axial direction.

Figure 3:
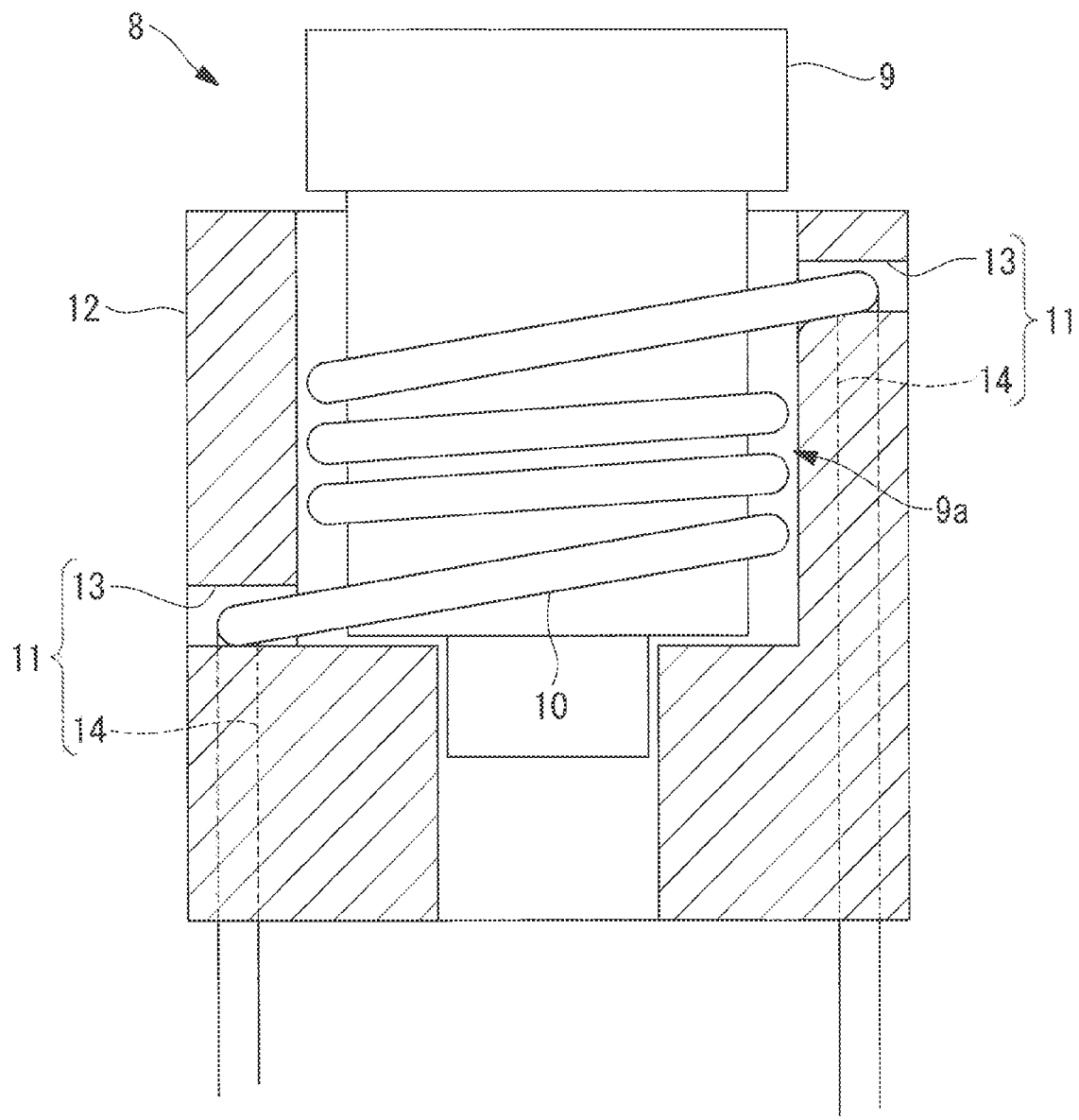
FIG. 3 is a vertical sectional view showing the detail of the rotation mechanism provided in the movable part in FIG. 2.
Figure 4:
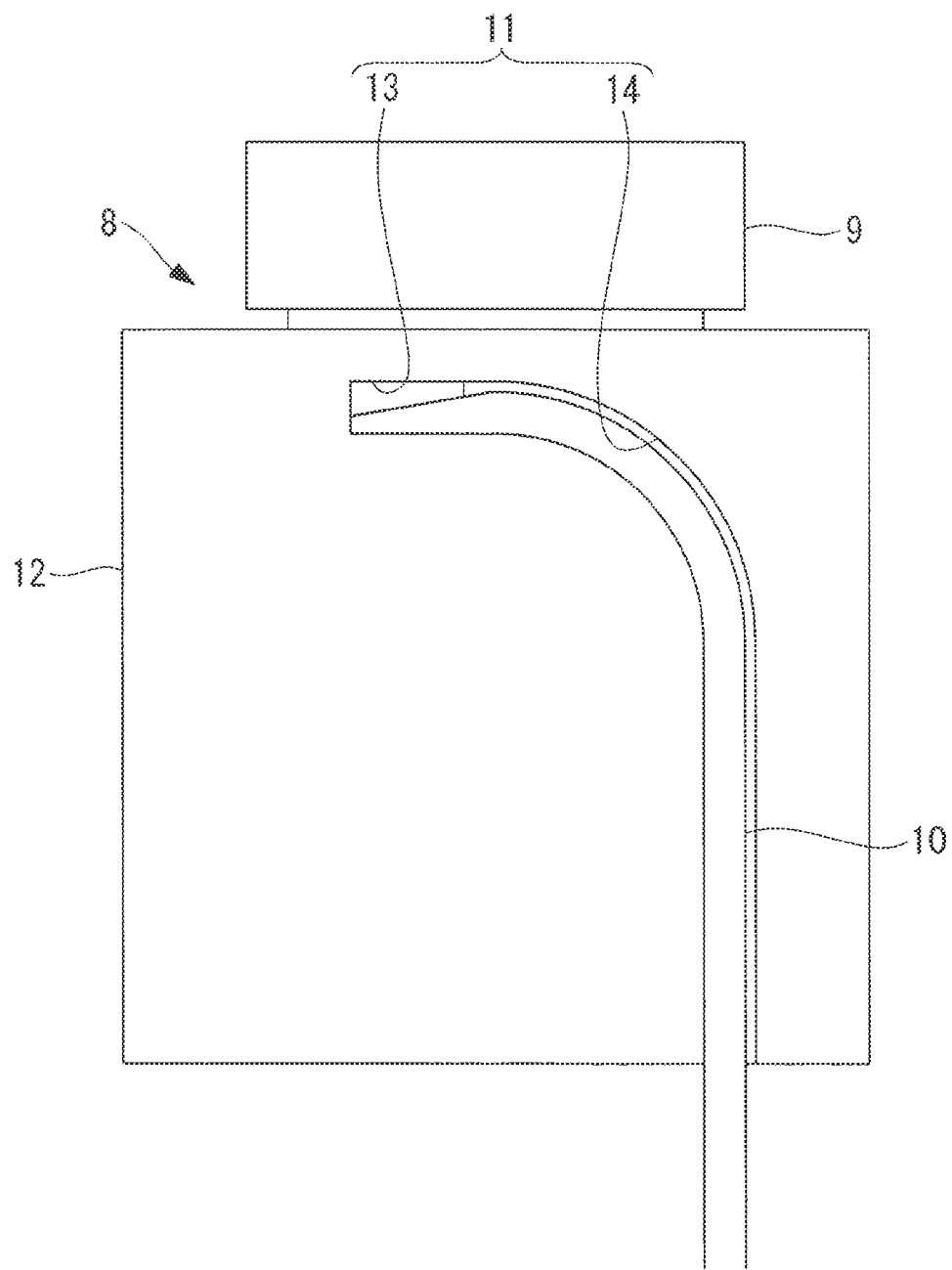
FIG. 4 is a side view of the rotation mechanism in FIG. 2.

As shown in FIGS. 3 and 4, the folding parts 11 include through-holes (inner holes) 13 provided in the housing 12 so as to allow the portions of the wire 10 led out in tangential directions from the rotator 9 at both sides of the wound part 9a in the axial direction to pass in the radial direction, and guide grooves 14 formed in the outer circumferential surface so as to guide the portions of the wire 10 passing through the through-holes 13 and led radially outward of the housing 12.

As shown in FIG. 4, the guide grooves 14 in the outer surface of the housing 12 extend in the circumferential direction from the through-holes 13, are bent toward the proximal-end side with a certain radius of curvature, and extend linearly toward the proximal-end side so as to be parallel to the longitudinal axis. With this configuration, the portions of the wire 10 led out in tangential directions from the rotator 9 pass through the through-holes 13, are bent with a certain radius of curvature along the guide grooves 14, and extend toward the proximal-end side.

The operation of the thus-configured rotation mechanism 8 of the medical manipulator 1 according to this embodiment will be described below.

In the rotation mechanism 8 according to this embodiment, when a tension to pull one portion of the wire 10 toward the proximal-end side is applied at the proximal-end side of the insertion part 2 by actuating the driving part 4, the tension is transmitted to the rotator 9 through the wire 10, rotating the rotator 9 in the direction of the torque applied by the portion of the wire 10 to which the tension is applied. Because the rotator 9 is fixed to the gripping part 7, it is possible to rotate the gripping part 7 about the longitudinal axis.

In this case, the wire 10 is spirally wound on the outer circumferential surface of the rotator 9 over a predetermined area in the longitudinal axis direction and is led out in tangential directions from both sides of the wound part 9a in the longitudinal axis direction. The portions of the wire 10 led out in tangential directions pass through the through-holes 13 in the folding parts 11, are led out radially outward of the housing 12, and are folded along the guide grooves 14. Accordingly, it is possible to reliably prevent contact between two portions of the wire 10 led out from the rotator 9, regardless of to which angular position the gripping part 7 is rotated about the longitudinal axis by pulling one of the portions. This leads to an advantage in that it is possible to prevent rubbing between the two portions of the wire 10 that rotates the gripping part 7 about the longitudinal axis, thus preventing lowering of the durability and operability thereof.

Furthermore, because the wire 10 to which the tension is applied is bent along the guide groove 14 provided in the outer surface of the housing 12 and is pulled toward the proximal-end side, the wire 10 is bent with a relatively large radius of curvature and is not subjected to intolerable bending stress. Thus, it is possible to improve the durability.

Figure 5:
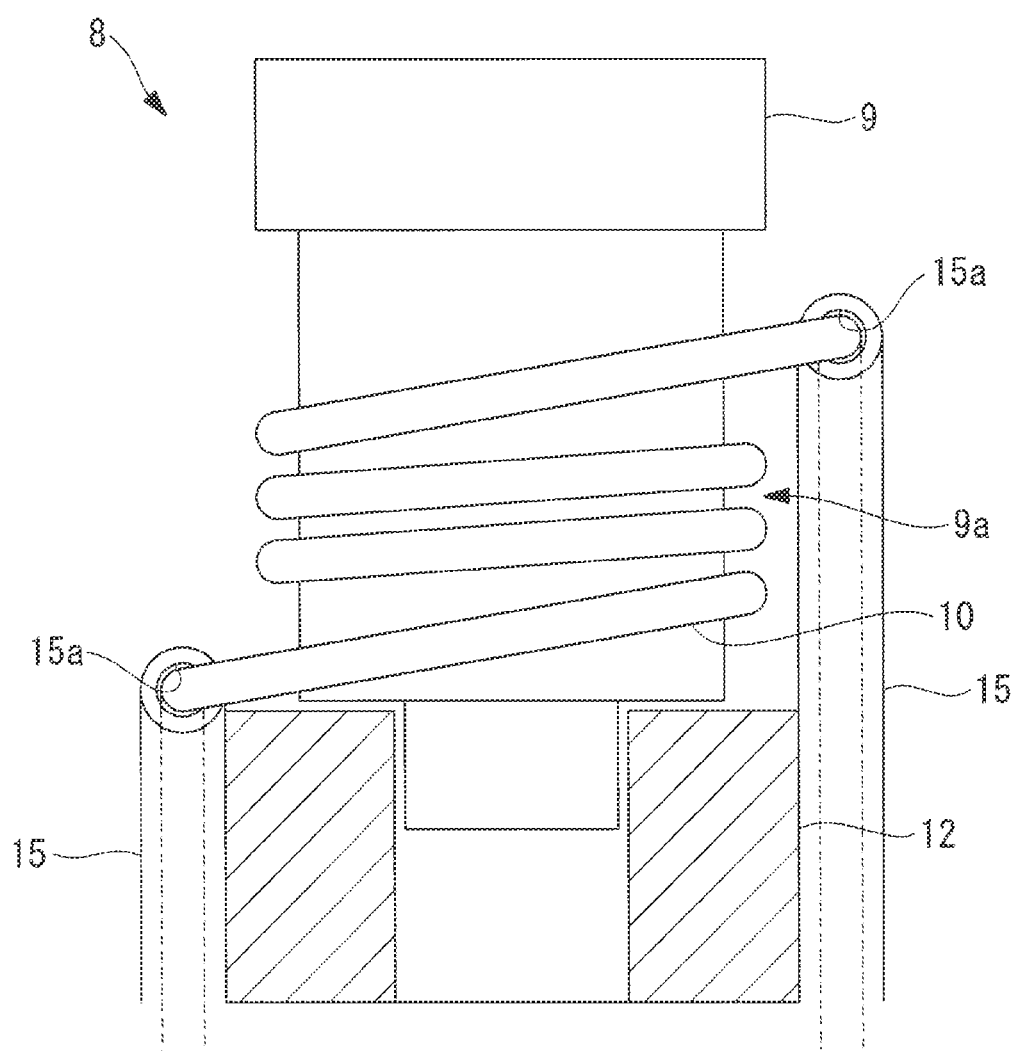
FIG. 5 is a vertical sectional view showing a first modification of the rotation mechanism in FIG. 2.

Note that, in this embodiment, the substantially cylindrical housing 12 surrounding the radially outer side of the rotator 9 is provided, and the folding parts 11 for folding the wire 10 are formed of the through-holes 13 and the guide grooves 14 provided in the housing 12. Instead of this, as shown in FIG. 5, tubular members (outer members) 15 that are disposed on the radially outer side of the rotator 9 and that are bent in the same shape as the guide grooves 14 in FIG. 4 may be employed as the folding parts 11. By allowing the two portions of the wire 10 led out in tangential directions from the rotator 9 to pass through inner holes (folding parts) 15a of the tubular members 15, the portions are guided toward the proximal-end side.

Figure 6:
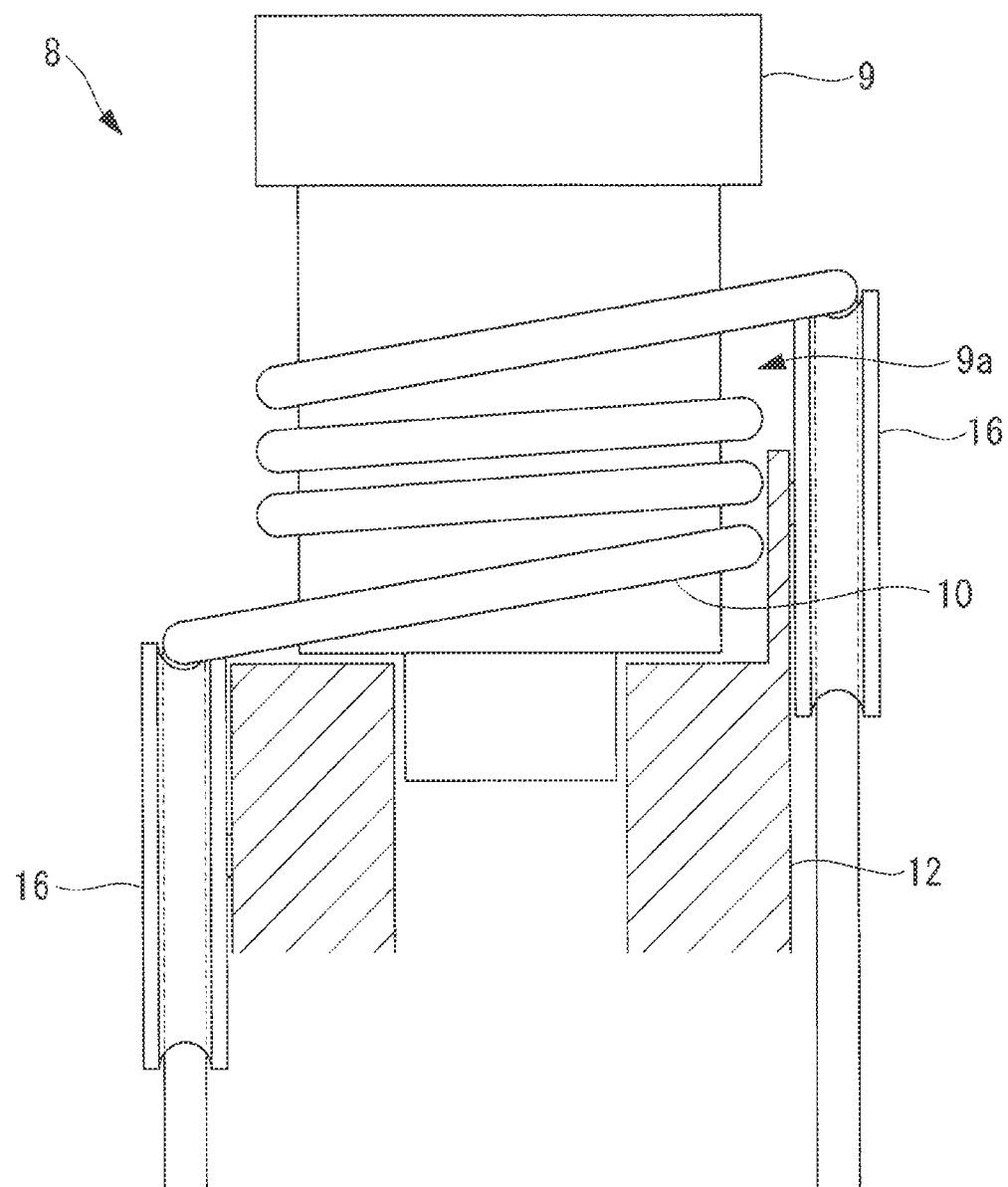
FIG. 6 is a vertical sectional view showing a second modification of the rotation mechanism in FIG. 2.

Furthermore, as shown in FIG. 6, pulleys 16 that have cylindrical guide surfaces for guiding the wire 10 and that are disposed on the radially outer side of the rotator 9 so as to be rotatable about an axis perpendicular to the longitudinal axis of the rotator 9 may be employed as the folding parts 11. By bending the two portions of the wire 10 led out in tangential directions from the rotator 9 by hooking them on the pulleys 16, the portions of the wire 10 are guided toward the proximal-end side. By rotating the pulleys 16, it is possible to reduce friction of the wire 10 at the folding parts 11, thus further improving the durability and operability.

Furthermore, instead of the pulleys 16, pins (not shown) that have cylindrical surfaces extending in a direction perpendicular to the longitudinal axis of the rotator 9 and located at the same positions as those of the pulleys 16 may be employed as the folding parts 11.

In the above-described embodiment, although the folding parts 11 are provided for the two portions of the wire 10 led out in tangential directions from the rotator 9, it is only necessary that the folding part 11 be provided for the portion of the wire 10 that is led out at, at least, the distal-end side in the longitudinal axis direction. Furthermore, when the folding parts 11 are provided for the two portions of the wire 10, different folding parts 11 may be provided for the two portions of the wire 10.

Figure 7:
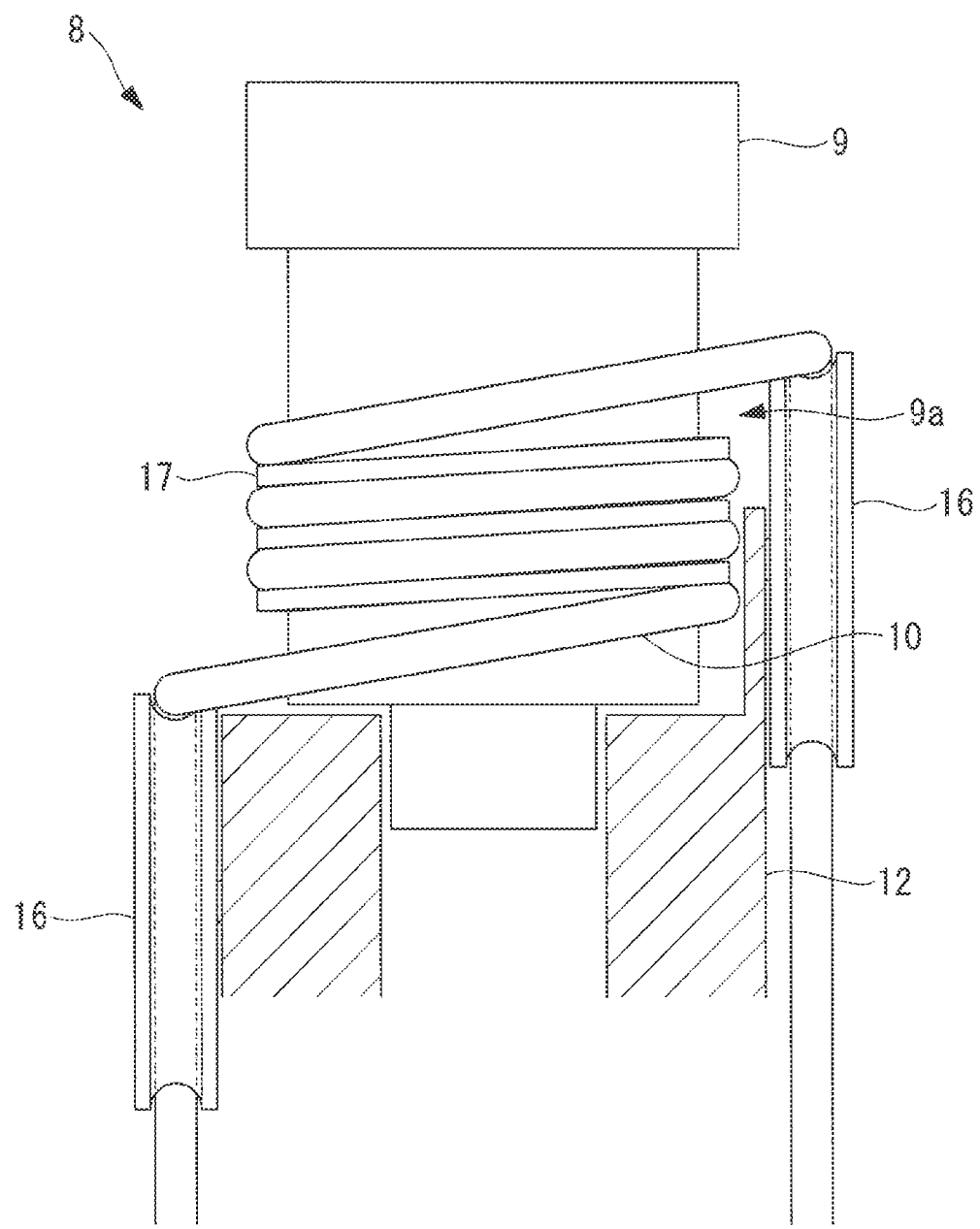
FIG. 7 is a vertical sectional view showing a third modification of the rotation mechanism in FIG. 2.

Furthermore, as shown in FIG. 7, a spiral projection 17 that serves as a partition to prevent contact between portions of the wire 10 wound around the wound part 9a of the rotator 9 at a certain pitch may be provided. By doing so, it is possible to prevent rubbing between portions of the wire 10 also in the wound part 9a. Note that, instead of the projection 17, a spiral groove (not shown) may be provided by forming a recess in the wound part 9a of the rotator 9, and the wire 10 may be accommodated in the groove.

The above-described embodiment leads to the following invention.

An aspect of the present invention is a medical-manipulator rotation mechanism including: a cylindrical rotator that is fixed to a treatment part at a distal end and that is supported so as to be rotatable about a longitudinal axis; a long power-transmitting member wound around the rotator; and a folding part that bends the power-transmitting member led out in a tangential direction from the rotator to guide the power-transmitting member toward a proximal-end side. The power-transmitting member is led out in tangential directions at different positions between which a wound part of the rotator around which the power-transmitting member is wound exists.

According to this aspect, when one end of the power-transmitting member wound around the rotator and led out in tangential directions from both sides of the wound part is pulled toward the proximal-end side, the tension applied thereto is transmitted through the power-transmitting member and acts on the rotator, rotating the rotator with a rotational force that is proportional to the radius of the rotator and the tension. As a result, it is possible to rotate, about the longitudinal axis, the treatment part provided at the distal end and fixed to the rotator.

In this case, because the power-transmitting member is led out in two tangential directions from different positions between which a wound part of the rotator around which the power-transmitting member is wound exists, it is possible to prevent contact between the led-out portions of the power-transmitting member, and thus, to prevent rubbing between the portions of the power-transmitting member to prevent lowering of the durability and operability thereof.

In the above aspect, the medical-manipulator rotation mechanism may further include an outer member that is disposed on the radially outer side of the rotator and that is rotatable about the longitudinal axis relative to the rotator. The folding part may be provided in the outer member.

With this configuration, because one of the portions of the power-transmitting member led out in tangential directions from the rotator is separated away from the rotator, as a result of the portion being guided to the folding part provided in the outer member located on the radially outer side of the rotator, it is possible to more reliably prevent rubbing between this portion and the portion of the power-transmitting member wound around the rotator.

Furthermore, in the above-described aspect, the folding part may be a guide groove that guides the power-transmitting member, the guide groove penetrating through the outer member in the radial direction and being provided in an outer surface of the outer member.

With this configuration, because one of the portions of the power-transmitting member led out in tangential directions from the rotator is folded by the guide groove penetrating through the outer member and formed in the outer surface, the portion is physically separated away from the portion of the power-transmitting member wound around the rotator. Thus, it is possible to more reliably prevent rubbing therebetween.

Furthermore, in the above-described aspect, the outer member may be a tubular member, and the folding part may be an inner hole in the outer member that guides the power-transmitting member by allowing the power-transmitting member to pass therethrough.

With this configuration, because one of the portions of the power-transmitting member led out in tangential directions from the rotator is allowed to pass through the inner hole in the outer member, which is a tubular member, the portion is physically separated away from the portion of the power-transmitting member wound around the rotator. Thus, it is possible to more reliably prevent rubbing therebetween.

Furthermore, in the above-described aspect, the folding part may be a pulley or a pin provided on the outer member, the pulley or the pin having a cylindrical guide surface that guides the power-transmitting member around an axis extending in a radial direction.

With this configuration, it is possible to form the folding part that does not forcibly bend the power-transmitting member from the cylindrical guide surface of the pulley or the pin, which has a simple configuration. Thus, it is possible to maintain the soundness of the power-transmitting member.

Furthermore, in the above-described aspect, a spiral projection or groove along which the power-transmitting member is wound at a certain pitch may be provided on an outer surface of the rotator.

With this configuration, even in the wound part, in which the power-transmitting member is wound around the rotator, it is possible to prevent rubbing between adjacent portions of the power-transmitting member, thus preventing lowering of the durability and operability thereof.

Furthermore, in the above-described aspect, the folding part may be provided at two positions so as to guide the power-transmitting member led out in tangential directions from both sides of the wound part in the longitudinal axis direction toward the proximal-end side.

With this configuration, it is possible to bend not only the portion of the power-transmitting member led out from the distal-end side of the wound part, but also the portion of the power-transmitting member led out from the proximal-end side of the wound part and to reliably guide these portions to the proximal-end side with the folding parts.

REFERENCE SIGNS LIST 1 medical manipulator
7 gripping part (treatment part)
8 rotation mechanism
9 rotator
9a wound part
10 wire (power-transmitting member)
11 folding part
12 housing (outer member)
13 through-hole (inner hole)
14 guide groove
15 tubular member (outer member)
15a inner hole (folding part)
16 pulley (folding part)
17 projection

The invention claimed is:

1. A medical-manipulator rotation mechanism comprising:
   a cylindrical rotator fixed to a treatment part at a distal end of the rotator, the rotator being supported so as to be rotatable about a longitudinal axis;
   an elongated power-transmitting member having first and second ends and a portion wound around the rotator; and
   a folding part that bends the first and second ends of the power-transmitting member in a tangential direction from the portion wound around the rotator and extends each of the first and second ends from the rotator toward a proximal-end side.

2. The medical-manipulator rotation mechanism according to claim 1, further comprising an outer member disposed on a radially outer side of the rotator, the outer member being rotatable about the longitudinal axis relative to the rotator,
   wherein the folding part is provided in the outer member.

3. The medical-manipulator rotation mechanism according to claim 2, wherein the folding part is a guide groove that guides the power-transmitting member, the guide groove penetrating through the outer member in a radial direction and being provided in an outer surface of the outer member.

4. The medical-manipulator rotation mechanism according to claim 2, wherein
   the outer member is a tubular member, and
   the folding part is an inner hole in the outer member that guides the power-transmitting member by allowing the power-transmitting member to pass therethrough.

5. The medical-manipulator rotation mechanism according to claim 2, wherein the folding part is a pulley or a pin provided on the outer member, the pulley or the pin having a cylindrical guide surface that guides the power-transmitting member around an axis extending in a radial direction.

6. The medical-manipulator rotation mechanism according to claim 1, wherein a spiral projection or groove along which the power-transmitting member is wound at a certain pitch is provided on an outer surface of the rotator.

7. The medical-manipulator rotation mechanism according to claim 1, wherein the folding part is configured such that each of the first and second ends of the power-transmitting member extend tangentially outward from the portion wound around the rotator at a different longitudinal position of the rotator.

8. The medical-manipulator rotation mechanism according to claim 1, wherein the first and second channels are configured such that each of the first and second ends of the wire extend tangentially outward from the portion wound around the rod at a different longitudinal position of the rod.

9. A medical-manipulator rotation mechanism comprising:
   a cylindrical rod fixed to a treatment part at a distal end of the rod, the rod being supported so as to be rotatable about a longitudinal axis;
   an elongated wire having first and second ends and a portion wound around the rod; and
   first and second channels that respectively bend the first and second ends of the wire in a tangential direction from the portion wound around the rotator and extend each of the first and second ends from the rod toward a proximal-end side.

10. A medical-manipulator comprising:
an elongated insertion part;
a rotation mechanism disposed at a distal end of the insertion part such that the rotation mechanism is rotatable relative to the distal end of the insertion part;
a driving part disposed at a proximal end of the insertion part; and
a treatment part disposed at a distal end of the rotation mechanism such that the treatment part is rotatable with the rotation mechanism;
the rotation mechanism comprising:
- a cylindrical rotator fixed to the treatment part at a distal end of the rotator, the rotator being supported in the distal end of the insertion part so as to be rotatable about a longitudinal axis;
- an elongated power-transmitting member having first and second ends and a portion wound around the rotator; and
- a folding part that bends the first and second ends of the power-transmitting member in a tangential direction from the portion wound around the rotator and extends each of the first and second ends from the rotator toward the driving part;

wherein each of the first and second ends of the power-transmitting member extend from the folding part to the driving part.

11. The medical-manipulator according to claim 10, wherein the folding part is configured such that each of the first and second ends of the power-transmitting member extend tangentially outward from the portion wound around the rotator at a different longitudinal position of the rotator.

* * * * *